US 11,448,872 B2

(12) United States Patent
Carpenter et al.

(10) Patent No.: US 11,448,872 B2
(45) Date of Patent: *Sep. 20, 2022

(54) LIGHT-ENHANCED SELF-CLEANING FILM SYSTEM AND METHOD OF FORMING SAME

(71) Applicant: GM GLOBAL TECHNOLOGY OPERATIONS LLC, Detroit, MI (US)

(72) Inventors: James A. Carpenter, Rochester Hills, MI (US); Thomas A. Seder, Fraser, MI (US); Gayatri V. Dadheech, Bloomfield Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 428 days.

This patent is subject to a terminal disclaimer.

(21) Appl. No.: 16/544,435

(22) Filed: Aug. 19, 2019

(65) Prior Publication Data

US 2019/0369389 A1 Dec. 5, 2019

Related U.S. Application Data

(63) Continuation of application No. 15/609,588, filed on May 31, 2017, now Pat. No. 10,429,641.

(51) Int. Cl.
*G02B 27/00* (2006.01)
*A61L 2/232* (2006.01)
(Continued)

(52) U.S. Cl.
CPC .......... *G02B 27/0006* (2013.01); *A61L 2/232* (2013.01); *B08B 7/005* (2013.01);
(Continued)

(58) Field of Classification Search
CPC .... G02B 1/18; G02B 27/0006; G02B 6/0068; B08B 17/02; B08B 7/0057; B08B 7/005; A61L 2/232
(Continued)

(56) References Cited

U.S. PATENT DOCUMENTS 4,047,804 A * 9/1977 Stephens ................ G03C 1/825
428/339
4,449,050 A 5/1984 Kamhi
(Continued)

FOREIGN PATENT DOCUMENTS

CN 201035171 Y 3/2008
CN 101422974 A 5/2009
(Continued)

OTHER PUBLICATIONS

Dadheech, Gayatri V. et al., U.S. Appl. No. 16/742,491, filed Jan. 14, 2020 entitled "Self-Cleaning Film System and Method of Forming Same," 31 pages.
(Continued)

*Primary Examiner* — David G Cormier
*Assistant Examiner* — Thomas Bucci
(74) *Attorney, Agent, or Firm* — Harness, Dickey & Pierce, P.L.C.

(57) ABSTRACT

A self-cleaning film system includes a substrate and a film. The film includes a monolayer formed from a fluorinated material, and a first plurality of regions disposed within the monolayer and spaced apart from one another such that each of the regions abuts, is surrounded by, and is not covered by the fluorinated material. Each of the regions includes a photocatalytic material. The system may include a wave guide disposed adjacent the substrate. The wave guide includes a first light source configured for emitting a first portion of electromagnetic radiation towards the film having an ultraviolet wavelength of from 10 nm to 400 nm, and a second light source configured for emitting a second portion of electromagnetic radiation towards the film having an infrared wavelength of from 700 nm to 1 mm. A method of forming a self-cleaning film system configured for reducing a visibility of a contaminant is disclosed.

19 Claims, 3 Drawing Sheets

(51) Int. Cl.
  *B08B 7/00* (2006.01)
  *B08B 17/02* (2006.01)
  *F21V 8/00* (2006.01)
  *G02B 1/18* (2015.01)

(52) U.S. Cl.
  CPC ............ *B08B 7/0057* (2013.01); *B08B 17/02* (2013.01); *G02B 1/18* (2015.01); *G02B 6/0068* (2013.01)

(58) Field of Classification Search
  USPC ..... 134/104.1, 56 R, 1, 19, 4; 427/162, 164, 427/180, 160; 428/421, 422, 432, 143
  See application file for complete search history.

(56) References Cited

U.S. PATENT DOCUMENTS

| | | | |
|---|---|---|---|
| 4,536,179 | A | 8/1985 | Anderson et al. |
| 4,915,981 | A | 4/1990 | Traskos et al. |
| 5,570,161 | A * | 10/1996 | Andrews ................. H04N 1/29 399/98 |
| 6,055,085 | A * | 4/2000 | Nakashima ......... C03C 17/2456 359/507 |
| 6,101,266 | A | 8/2000 | Laskowski et al. |
| 6,193,378 | B1 * | 2/2001 | Tonar ..................... B60R 1/088 359/603 |
| 6,406,158 | B1 | 6/2002 | Ohkawa |
| 6,797,974 | B2 | 9/2004 | Philipp et al. |
| 6,816,297 | B1 * | 11/2004 | Tonar ....................... G02B 1/14 359/507 |
| 7,359,543 | B2 | 4/2008 | Tsuji et al. |
| 8,047,426 | B2 | 11/2011 | Haycock et al. |
| 9,044,574 | B2 | 6/2015 | Yoshimachi |
| 9,259,513 | B2 | 2/2016 | Bedwell et al. |
| 9,468,088 | B2 | 10/2016 | Nah |
| 9,611,016 | B2 | 4/2017 | Salters et al. |
| 9,861,974 | B2 | 1/2018 | Dadheech et al. |
| 10,052,622 | B2 | 8/2018 | Dadheech et al. |
| 10,195,602 | B2 | 2/2019 | Dadheech et al. |
| 10,274,647 | B2 | 4/2019 | Seder et al. |
| 10,429,641 | B2 * | 10/2019 | Carpenter ............... B08B 17/02 |
| 10,533,249 | B2 | 1/2020 | Dadheech et al. |
| 10,556,231 | B2 | 2/2020 | Dadheech et al. |
| 10,569,263 | B2 | 2/2020 | Dadheech et al. |
| 10,583,428 | B2 | 3/2020 | Seder et al. |
| 10,754,067 | B2 | 8/2020 | Seder et al. |
| 2005/0049158 | A1 * | 3/2005 | Cai ........................... C09D 4/00 510/197 |
| 2005/0186871 | A1 | 8/2005 | Hockaday |
| 2005/0191505 | A1 | 9/2005 | Akarsu et al. |
| 2006/0137708 | A1 * | 6/2006 | Ghosh .................... B01J 19/123 134/1 |
| 2006/0150862 | A1 | 7/2006 | Zhao et al. |
| 2006/0276360 | A1 * | 12/2006 | Muradov .................. C11D 7/16 510/240 |
| 2007/0114121 | A1 * | 5/2007 | Kinlen ...................... A61L 2/03 423/584 |
| 2007/0218264 | A1 * | 9/2007 | Gueneau ............. C03C 17/3435 351/159.62 |
| 2007/0237943 | A1 | 10/2007 | Wakizaka et al. |
| 2007/0248790 | A1 * | 10/2007 | Ogata ................... C04B 41/009 428/98 |
| 2008/0053308 | A1 * | 3/2008 | Marzolin ............... B01J 35/004 427/595 |
| 2009/0045617 | A1 * | 2/2009 | Lawandy .............. C09D 11/037 283/67 |
| 2009/0130608 | A1 | 5/2009 | Irving et al. |
| 2009/0196791 | A1 * | 8/2009 | Ogata ..................... C02F 1/4602 556/400 |
| 2009/0267015 | A1 * | 10/2009 | Ogata ..................... B08B 17/02 252/62.3 R |
| 2010/0028604 | A1 | 2/2010 | Bhushan et al. |
| 2010/0128965 | A1 | 5/2010 | Blair |
| 2010/0326699 | A1 * | 12/2010 | Greyling .................. H01B 3/47 977/773 |
| 2011/0121634 | A1 * | 5/2011 | Koike ..................... B32B 7/025 301/5.1 |
| 2011/0200656 | A1 * | 8/2011 | Olsson ................... B42D 25/29 424/405 |
| 2011/0220855 | A1 | 9/2011 | Weir et al. |
| 2012/0009429 | A1 * | 1/2012 | Shmueli ................... C09D 5/006 106/286.6 |
| 2012/0148832 | A1 * | 6/2012 | Yabuta ................... B01J 21/063 428/331 |
| 2013/0087374 | A1 * | 4/2013 | Nah ...................... H05K 1/0213 427/126.3 |
| 2014/0083473 | A1 * | 3/2014 | Lawandy ............... D21H 21/36 977/773 |
| 2014/0147654 | A1 | 5/2014 | Walther et al. |
| 2015/0004398 | A1 * | 1/2015 | Yabuta ................... B01J 35/004 428/328 |
| 2015/0164081 | A1 * | 6/2015 | Ryan ....................... A01N 59/00 428/432 |
| 2015/0238644 | A1 | 8/2015 | Sung et al. |
| 2015/0284592 | A1 * | 10/2015 | Gorun .................... B01J 35/004 524/88 |
| 2016/0107204 | A1 | 4/2016 | Lawandy |
| 2017/0056871 | A1 * | 3/2017 | Dadheech ................. F01N 3/00 |
| 2017/0232430 | A1 * | 8/2017 | Dadheech ............... B01J 35/06 502/4 |
| 2018/0154345 | A1 * | 6/2018 | Dadheech ............... B01J 21/04 |
| 2018/0318820 | A1 | 11/2018 | Dadheech et al. |
| 2018/0320023 | A1 | 11/2018 | Dadheech et al. |
| 2018/0333709 | A1 | 11/2018 | Seder et al. |
| 2018/0333710 | A1 | 11/2018 | Dadheech et al. |
| 2018/0333711 | A1 | 11/2018 | Dadheech et al. |
| 2018/0333756 | A1 | 11/2018 | Seder et al. |
| 2018/0334742 | A1 | 11/2018 | Dadheech et al. |
| 2018/0335548 | A1 | 11/2018 | Seder et al. |
| 2018/0348509 | A1 | 12/2018 | Carpenter et al. |
| 2020/0147598 | A1 | 5/2020 | Dadheech et al. |
| 2020/0200946 | A1 | 6/2020 | Seder et al. |

FOREIGN PATENT DOCUMENTS

| | | |
|---|---|---|
| CN | 101868762 A | 10/2010 |
| CN | 102998723 A | 3/2013 |
| CN | 103241961 A | 8/2013 |
| CN | 103740292 A | 4/2014 |
| CN | 103950248 A | 7/2014 |
| CN | 105038438 A | 11/2015 |
| CN | 106477901 A | 3/2017 |
| CN | 106569637 A | 4/2017 |
| CN | 106633158 A | 5/2017 |
| CN | 107083184 A | 8/2017 |
| CN | 108948889 A | 12/2018 |
| CN | 108949031 A | 12/2018 |
| CN | 108949050 A | 12/2018 |
| CN | 108953597 A | 12/2018 |
| CN | 108953598 A | 12/2018 |
| CN | 108976873 A | 12/2018 |
| DE | 102016116007 A1 | 3/2017 |
| DE | 102018111826 A1 | 11/2018 |
| DE | 102018111827 A1 | 11/2018 |
| DE | 102018111828 A1 | 11/2018 |
| DE | 102018111830 A1 | 11/2018 |
| DE | 102018111831 A1 | 11/2018 |
| DE | 102018112987 A1 | 12/2018 |
| JP | S63308920 | 12/1988 |
| KR | 20160012190 A | 2/2016 |
| WO | 2005077556 A1 | 8/2005 |
| WO | 2011123373 A1 | 10/2011 |
| WO | 2015194200 A1 | 12/2015 |

OTHER PUBLICATIONS

First Office Action for Chinese Patent Application No. 201810443424.3 dated Oct. 9, 2019 with English language machine translation, 11 pages.

(56) References Cited

OTHER PUBLICATIONS

First Office Action for Chinese Patent Application No. 201810440683.0 dated Oct. 18, 2019 with English language machine translation, 14 pages.
First Office Action for Chinese Patent Application No. 201810465452.5 dated Feb. 3, 2020 with English language machine translation, 21 pages.
Seder, Thomas A. et al., U.S. Appl. No. 16/809,056, filed Mar. 4, 2020 entitled, "Textured Self-Cleaning Film System and Method of Forming Same," 31 pages.
First Office Action for Chinese Patent Application No. 201810440411.0 dated Mar. 4, 2020 with English language machine translation, 21 pages.
First Office Action for Chinese Patent Application No. 201810435135.9 dated Mar. 12, 2020 with English language machine translation, 18 pages.
Kin, Zhong et al., "Research progress of fabrication and application of superamphiphobic surface," Chemical Industry and Engineering Progress, 2, pp. 447-455, 478 (2015) (Abstract Only).
U.S. Appl. No. 15/609,588, filed May 31, 2017.
English language machine translation provided by Espacenet for CN 108949031 A. Further, U.S. Publication No. 2018/0334742 is believed to be an English language equivalent of CN 108949031 A.
English language machine translation provided by Espacenet for CN 108949050 A. Further, U.S. Publication No. 2018/0335548 is believed to be an English language equivalent of CN 108949050 A.
English language machine translation provided by Espacenet for CN 108953597 A. Further, U.S. Publication No. 2018/0333709 is believed to be an English language equivalent of CN 108953597 A.
English language machine translation provided by Espacenet for CN 108953598 A. Further, U.S. Publication No. 2018/0333710 is believed to be an English language equivalent of CN 108953598 A.
English language machine translation provided by Espacenet for CN 108976873 A. Further, U.S. Publication No. 2018/0348509 is believed to be an English language equivalent of CN 108976873 A.
English language machine translation provided by Espacenet for DE 102018111826 A1. Furhter, U.S. Publication No. 2018/0333709 is believed to be an English language equivalent of DE 102018111826 A1.
English language machine translation provided by Espacenet for DE 102018111827 A1. Further, U.S. Publication No. 2018/0333756 is believed to be an English language equivalent of DE 102018111827 A1.
English language machine translation provided by Espacenet for DE 102018111828 A1. Further, U.S. Publication No. 2018/0335548 is believed to be an English language equivalent of DE 102018111828 A1.
English language machine translation provided by Espacenet for DE 102018111830 A1. Further, U.S. Publication No. 2018/0333710 is believed to be an English language equivalent of DE 102018111830 A1.
English language machine translation provided by Espacenet for DE 102018111831 A1. Further, U.S. Publication No. 2018/0334742 is believed to be an English language equivalent of DE 102018111831 A1.
English language machine translation provided by Espacenet for DE 102018112987 A1. Further, U.S. Publication No. 2018/0348509 is believed to be an English language equivalent of DE 102018112987 A1.
Science Mission Directorate, "Visible Light," NASA Science 2010, National Aeronautics and Space Administration; <http://science.nasa.gov/ems/09_visiblelight>.
Chen Qixing, Communication Principle, National Defense Industry Press, Jan. 2017; ISBN: 978-7-1181-1055-5.
Chen Ruoyun, Chinese edible medicinal fungal chemistry, Shanghai Science and Technology Literature Press, Mar. 2016; ISBN: 978-7-5439-6915-5.
First Office Action for Chinese Patent Application No. 201810437022.2 dated Jun. 3, 2020 with English language machine translation, 16 pages.
Second Office Action for Chinese Patent Application No. 201810443424.3 dated Jun. 28, 2020 with English language machine translation, 14 pages.
Second Office Action for Chinese Patent Application No. 201810465452.5 dated Aug. 5, 2020 with English anguage machine translation, 12 pages.
Third Office Action for Chinese Patent Application No. 201810443424.3 dated Feb. 9, 2021, with correspondence dated Feb. 17, 2021, from China Patent Agent (H.K.) Ltd. summarizing contents; 9 pages.
First Office Action for German Patent Application No. 102018112987.4 dated Dec. 2, 2020, with correspondence dated Dec. 23, 2020, from Manitz Finsterwald Patent-und.; 9 pages.

* cited by examiner

LIGHT-ENHANCED SELF-CLEANING FILM SYSTEM AND METHOD OF FORMING SAME

CROSS-REFERENCE TO RELATED APPLICATIONS

This application is a continuation of U.S. patent application Ser. No. 15/609,588 filed on May 31, 2017. The entire disclosure of the above application is incorporated herein by reference.

INTRODUCTION

The disclosure relates to a self-cleaning film system and to a method of forming the self-cleaning film system.

Devices, such as display systems, are often designed to be touched by an operator. For example, a vehicle may include a display system that presents information to an operator via a touchscreen. Similarly, an automated teller machine or kiosk may include a display system that is activated by touch.

Other devices, such as cameras and eyeglasses, generally include a lens surface which may be inadvertently touched by an operator during use. Further, other devices such as vehicles, windows, appliances, mirrors, appliances, cabinetry, furniture, cellular telephones, fingerprint scanners, sensors, copiers, medical instruments, and countertops may also include one or more surfaces which may be touched by an operator. Therefore, during use, an operator may deposit fingerprints and/or oils onto such devices and surfaces.

SUMMARY

A self-cleaning film system includes a substrate and a film disposed on the substrate. The film includes a monolayer formed from a fluorinated material selected from the group consisting of fluorinated organic compounds, fluorinated inorganic compounds, and combinations thereof. The film also includes a first plurality of regions disposed within the monolayer and spaced apart from one another such that each of the first plurality of regions abuts, is surrounded by, and is not covered by the fluorinated material. Each of the first plurality of regions includes a photocatalytic material. The self-cleaning film system also optionally includes a wave guide disposed adjacent the substrate. The wave guide may include a first light source configured for emitting a first portion of electromagnetic radiation towards the film. The first portion of electromagnetic radiation has an ultraviolet wavelength of from 10 nm to 400 nm. The wave guide also includes a second light source configured for emitting a second portion of electromagnetic radiation towards the film. The second portion of electromagnetic radiation has an infrared wavelength of from 700 nm to 1 mm.

In one aspect, the film may have a first surface and a second surface spaced opposite the first surface and abutting the substrate. The first surface may be substantially free from squalene.

In one aspect, the substrate may have a proximal surface abutting the second surface, a distal surface spaced opposite the proximal surface, a first edge connecting the proximal surface and the distal surface, and a second edge spaced opposite the first edge. The wave guide may be disposed adjacent the first edge.

In another aspect, the self-cleaning film system may further include a dielectric coating disposed on the distal surface and configured for reflecting the first portion of electromagnetic radiation towards the proximal surface. The self-cleaning film system may also include an optical cement disposed between the substrate and the wave guide such that the wave guide is adhered to the substrate. The wave guide may further include a diffuser disposed at the substrate and configured for diffusing the first portion of electromagnetic radiation and the second portion of electromagnetic radiation. The first light source may include a plurality of ultraviolet photodiodes and the second light source may include a plurality of infrared photodiodes.

Further, the film may define a contact angle with water of greater than 140°.

In one aspect, the photocatalytic material may be titanium dioxide and may be present in the first plurality of regions in a rutile form. In another aspect, the photocatalytic material may be titanium dioxide and may be present in the first plurality of regions in an anatase form. In a further aspect, the photocatalytic material may be titanium dioxide and may be present in the first plurality of regions as a combination of a rutile form and an anatase form. In yet another aspect, the photocatalytic material may be doped with silver. The substrate may be formed from silicon dioxide.

In another aspect, the self-cleaning film system may include a second plurality of regions disposed within the monolayer such that each of the second plurality of regions abuts and is surrounded by the fluorinated material, wherein each of the second plurality of regions includes silver.

In one embodiment, the self-cleaning film system includes a substrate and a film disposed on the substrate. The film includes a monolayer formed from a fluorinated material selected from the group consisting of fluorinated organic compounds, fluorinated inorganic compounds, and combinations thereof. The film also includes a first plurality of regions disposed within the monolayer and spaced apart from one another such that each of the first plurality of regions abuts, is surrounded by, and is not covered by the fluorinated material. Each of the first plurality of regions includes a photocatalytic material. The self-cleaning film system also optionally includes a wave guide disposed adjacent the substrate. The wave guide may include a first light source configured for emitting a first portion of electromagnetic radiation towards the film, wherein the first portion of electromagnetic radiation has an ultraviolet wavelength of from 10 nm to 400 nm. The wave guide also includes a second light source configured for emitting a second portion of electromagnetic radiation towards the film having an infrared wavelength of from 700 nm to 1 mm. The self-cleaning film system also may include a display configured for emitting a ray of light towards the substrate. In addition, the self-cleaning film system can include a dielectric coating sandwiched between the substrate and the display and configured for reflecting the first portion of electromagnetic radiation towards the film.

In one aspect, the self-cleaning film system may also include a third light source disposed adjacent the display and configured for emitting a third portion of electromagnetic radiation towards the display. The third portion of electromagnetic radiation may have a wavelength of from 400 nm to 100 nm. In another aspect, the third portion of electromagnetic radiation may have a wavelength of from 740 nm to 380 nm.

A method of forming a self-cleaning film system configured for reducing a visibility of a contaminant includes depositing a monolayer formed from a fluorinated material selected from the group consisting of fluorinated organic compounds, fluorinated inorganic compounds, and combinations thereof onto a substrate. After depositing, the method includes ablating the monolayer to define a first plurality of cavities therein. Each of the first plurality of cavities is spaced apart from an adjacent one of the first plurality of cavities along the monolayer. After ablating, the method includes embedding a photocatalytic material into each of the first plurality of cavities to form a film on the substrate and thereby form the self-cleaning film system. The film includes a first plurality of regions including the photocatalytic material. The first plurality of regions are disposed within the monolayer and spaced apart from one another such that each of the first plurality of regions abuts, is surrounded by, and is not covered by the fluorinated material. The self-cleaning film system further includes a wave guide disposed adjacent the substrate and including a first light source configured for emitting a first portion of electromagnetic radiation towards the film, wherein the first portion of electromagnetic radiation has an ultraviolet wavelength of from 10 nm to 400 nm, and a second light source configured for emitting a second portion of electromagnetic radiation towards the film, wherein the second portion of electromagnetic radiation has an infrared wavelength of from 700 nm to 1 mm. The method also includes, after embedding, irradiating the film with the second portion of electromagnetic radiation to thereby move the contaminant towards the first plurality of regions, and irradiating the substrate with the first portion of electromagnetic radiation to thereby increase a photocatalytic degradation of the contaminant at the first plurality of regions and reduce the visibility of the contaminant.

In one aspect, the contaminant may include at least one methyl group, and irradiating may include at least one of stretching, deforming, and rocking the methyl group so that the contaminant translates along the film.

The above features and advantages and other features and advantages of the present disclosure will be readily apparent from the following detailed description of the preferred embodiments and best modes for carrying out the present disclosure when taken in connection with the accompanying drawings and appended claims.

DRAWINGS

DETAILED DESCRIPTION

Figure 1:
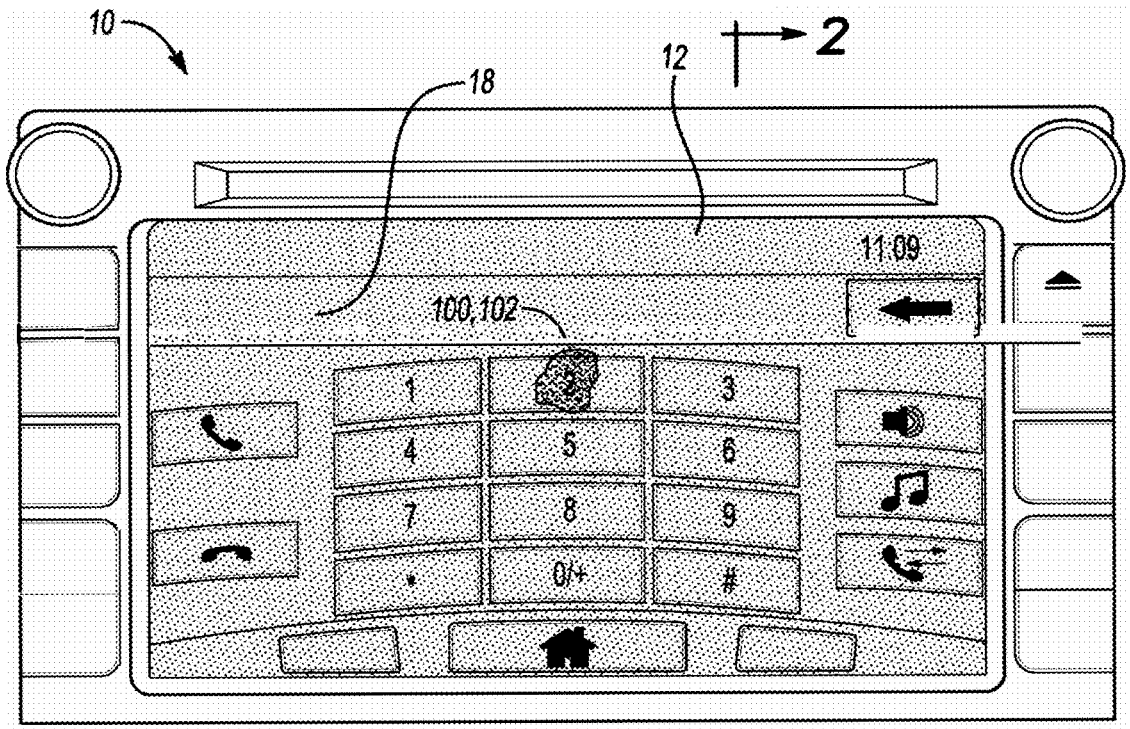
FIG. 1 is a schematic illustration of a front view of a self-cleaning film system.

Referring to the Figures, wherein like reference numerals refer to like elements, a self-cleaning film system 10 is shown generally in FIG. 1. The self-cleaning film system 10 is configured for reducing a visibility or conspicuity of a contaminant 100. For example, the self-cleaning film system 10 may be suitable for applications in which an operator may touch and deposit fingerprints, oils, and/or other organic or carbon-based contaminants 100 or pathogens onto a screen, lens, or surface. More specifically, the self-cleaning film system 10 may be useful for applications requiring a clean, substantially fingerprint-free screen, lens, or surface. That is, the self-cleaning film system 10 may be useful for removing fingerprints and other organic contaminants 100 from such screens, lenses, or surfaces.

For example, the self-cleaning film system 10 may be useful for automotive applications such as in-dash navigation systems which include a touchscreen, or vehicle cameras which include a lens. Alternatively, the self-cleaning film system 10 may be useful for non-automotive applications such as, but not limited to, consumer electronics, cellular telephones, eyewear, personal protective equipment, appliances, furniture, kiosks, fingerprint scanners, medical devices, sensors, aircraft, and industrial vehicles.

Figure 2:
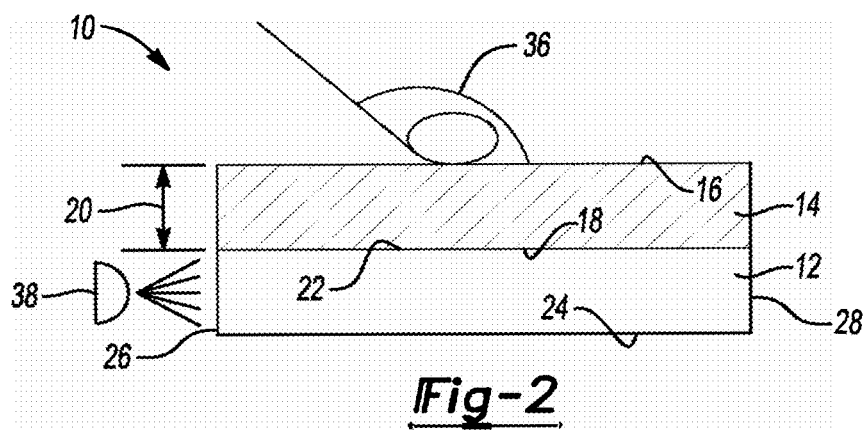
FIG. 2 is a schematic illustration of a cross-sectional view of the self-cleaning film system of FIG. 1 taken along section line 2-2.

Referring now to FIG. 2, the self-cleaning film system 10 includes a substrate 12. The substrate 12 may be formed from a vitreous, transparent material suitable for refracting visible light. For example, in one embodiment, the substrate 12 may be formed from silicon dioxide. In another example, the substrate 12 may be formed from a polycarbonate or other plastic. The substrate 12 may be configured as, by way of non-limiting examples, a screen of a display system, a lens of eyeglasses or goggles, a visor of a helmet, a surface of a refrigerator, a face of a cabinet, a door panel of a vehicle, a touchscreen of a kiosk, or as another surface or device that may be touched by an operator.

The self-cleaning film system 10 also includes a film 14 disposed on the substrate 12, e.g., chemically bonded to the substrate 12 as set forth in more detail below. The film 14 may be configured to cover and protect the substrate 12 from fingerprints, oils, pathogens, and organic contaminants 100 (FIG. 1). That is, the film 14 may be configured to cause fingerprints, oils, pathogens, and organic contaminants 100 deposited on the film 14 to vanish, disappear, or vaporize so as to maintain a clean substrate 12 that is capable of displaying crisp images or reflections.

More specifically, as described with reference to FIG. 2, the film 14 may have a first surface 16 and a second surface 18 spaced opposite the first surface 16. The second surface 18 may abut the substrate 12, and the first surface 16 may be substantially free from contaminants 100 (FIG. 1) such as squalene, organic material, and/or other oils of fatty acids. As used herein, the terminology squalene refers to an organic compound having 30 carbon atoms and represented by the International Union of Pure and Applied Chemistry name (6E,10E,14E,18E)-2,6,10,15,19,23-hexamethyltetracosa-2,6,10,14,18,22-hexaene. That is, the contaminant 100 may have at least one methyl group 102 (FIG. 1). In general, the film 14 may be characterized as a thin film and may have a thickness 20 of, for example, from 10 µm to 150 µm.

The substrate 12 may have a proximal surface 22 abutting the second surface 18 and a distal surface 24 spaced opposite the proximal surface 22. Therefore, the substrate 12 and the film 14 are configured to transmit visible light through the proximal surface 22, the distal surface 24, the first surface 16, and the second surface 18. The substrate 12 may also have a first edge 26 connecting the proximal surface 22 and the distal surface 24, and a second edge 28 spaced opposite the first edge 26. In some embodiments, the substrate 12 may also include an anti-reflection film (not shown). The anti-reflection film may be configured for reducing a reflection off the self-cleaning film system 10 and thereby improving an efficiency of the self-cleaning film system 10 since lost light in the system 10 may be minimized. As such, the self-cleaning film system 10 has both self-cleaning capabilities and comparatively low reflectance. Although not shown, the anti-reflection film may be formed from an anti-reflection coating comprising alternating layers of silicon dioxide and titanium dioxide.

Figure 3:
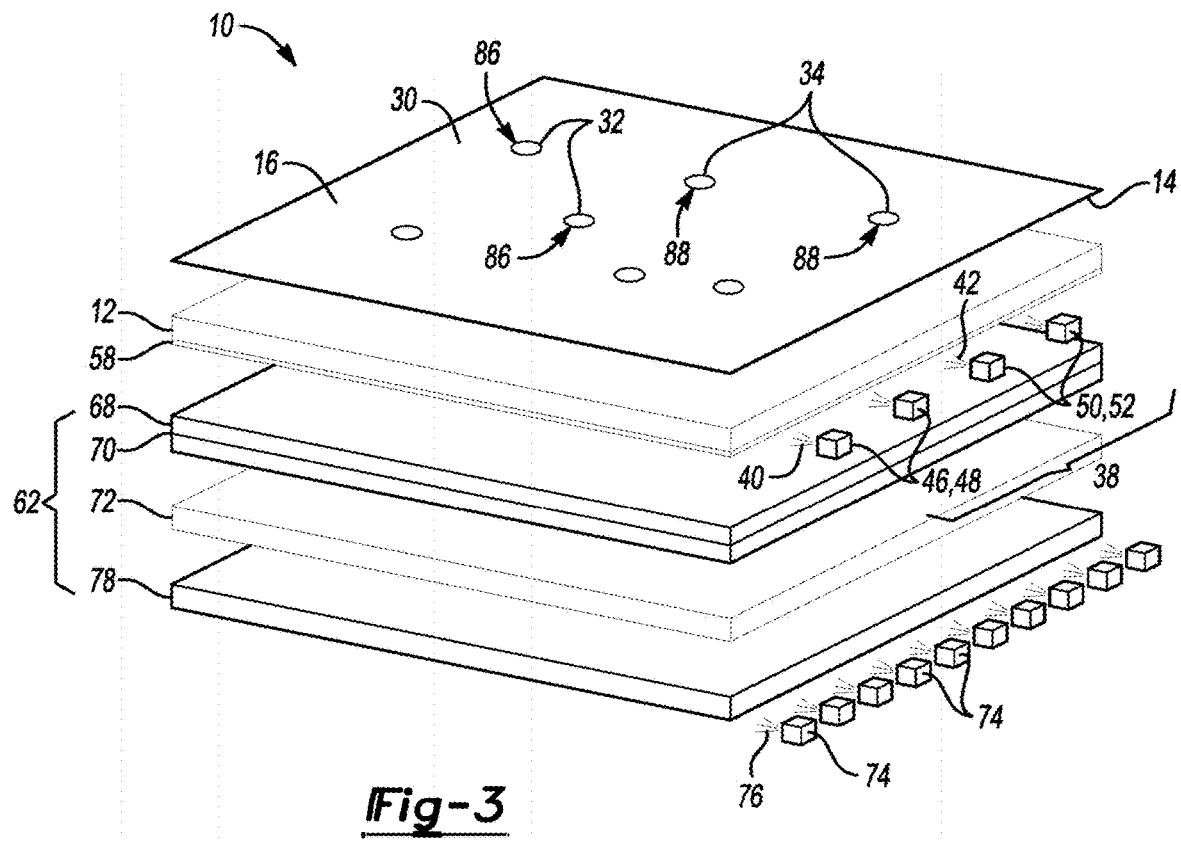
FIG. 3 is a schematic illustration of an exploded perspective view of one embodiment of the self-cleaning film system of FIGS. 1 and 2.

Referring now to FIG. 3, the film 14 includes a monolayer 30 formed from a fluorinated material selected from the group consisting of fluorinated organic compounds, fluorinated inorganic compounds, and combinations thereof. The monolayer 30 may form a majority of the film 14 and may be characterized as a monolayer field. As used herein, the terminology monolayer refers to a layer having a thickness 20 (FIG. 2) of one molecule. That is, the monolayer 30 is one molecule thick and may be characterized as a thin layer. In one embodiment, the fluorinated material may be fluorinated diamond-like carbon. In another embodiment, the fluorinated material may be fluorinated tin (IV) oxide. The fluorinated material, i.e., fluorinated organic compounds, fluorinated inorganic compounds, and combinations thereof, provides the film 14 with superhydrophobicity, anti-microbial properties, anti-soiling properties, and scratch-resistance. The film 14 may also contribute to a clean air quality of an ambient environment in which the film 14 is used.

As shown in FIG. 3, the film 14 also includes a first plurality of regions 32 disposed within the monolayer 30 and spaced apart from one another such that each of the first plurality of regions 32 abuts, is surrounded by, and is not covered by the fluorinated material. That is, the first plurality of regions 32 may be situated within and along the monolayer 30. In one embodiment, the first plurality of regions 32 may be equally spaced apart from each other along the first surface 16 (FIG. 2). In other embodiments, the first plurality of regions 32 may be randomly spaced throughout the monolayer 30 along the first surface 16. In still other embodiments, the first plurality of regions 32 may be arranged in a pattern within the monolayer 30. The first plurality of regions 32 may be present in the film 14 in an amount of from about 10 parts by volume to about 85 parts by volume based on 100 parts by volume of the film 14, e.g., about 50 parts by volume based on 100 parts by volume of the film 14.

Each of the first plurality of regions 32 includes a photocatalytic material, such as titanium dioxide. The photocatalytic material may provide the film 14 with self-cleaning capability. That is, the photocatalytic material may oxidize and/or vaporize the contaminant 100 (FIG. 1), e.g., organic material or squalene, present on the first surface 16 of the film 14, as set forth in more detail below. In particular, the photocatalytic material may be a light-activated photocatalyst upon exposure to, for example, visible, infrared, or ultraviolet light.

Suitable photocatalytic materials may include, but are not limited to, photo-oxidative semiconductors, semiconducting oxides, doped metal oxides, heterojunction materials, and combinations thereof.

In one embodiment, the photocatalytic material may be titanium dioxide and may be present in the first plurality of regions 32 in a rutile form. Alternatively, the photocatalytic material may be titanium dioxide and may be present in the first plurality of regions 32 in an anatase form, which may exhibit a comparatively higher photocatalytic activity than the rutile form. In other embodiments, the photocatalytic material may be titanium dioxide and may be present in the first plurality of regions 32 as a combination of the rutile form and the anatase form. Further, the photocatalytic material may be doped to form a functionalized photocatalytic material, e.g., functionalized titanium dioxide. For example, the functionalized photocatalytic material may be doped with a metal such as, but not limited to, chromium, cobalt, tungsten, copper, vanadium, iron, silver, platinum, molybdenum, lanthanum, niobium, and combinations thereof. Alternatively, the functionalized photocatalytic material may be doped with a non-metal such as, but not limited to, nitrogen, sulfur, carbon, boron, potassium, iodine, fluorine, and combinations thereof. In one example, the photocatalytic material may be doped with silver. Doping the photocatalytic material may increase a solar response of the photocatalytic material, may provide a comparatively higher photon abundance, and may increase a photo-activity of the photocatalytic material.

The photocatalytic material may be characterized as a nanoparticle and may have an average diameter measureable on a nanometer scale. Alternatively, the photocatalytic material may be characterized as a particle and may have an average diameter measureable on a micrometer scale. The photocatalytic material may have a thickness (not shown) of from 1 μm to 10 μm. Generally, the photocatalytic material may be present in the film 14 in an amount of from about 2 parts by volume to about 35 parts by volume based on 100 parts by volume of the film 14.

In other non-limiting embodiments, the first plurality of regions 32 may include a semiconducting oxide such as, but not limited to, zinc oxide, bismuth, tin oxide, and combinations thereof. The semiconducting oxide may be selected to have a band gap separation suitable for a photocatalytic reaction, as set forth in more detail below.

In another embodiment described with reference to FIG. 3, the film 14 may include a second plurality of regions 34 disposed within the monolayer 30 such that each of the second plurality of regions 34 abuts and is surrounded by the fluorinated material, wherein each of the second plurality of regions 34 includes silver. The second plurality of regions 34 may not be covered by the fluorinated material.

That is, the second plurality of regions 34 may also be situated within and along the monolayer 30. In one embodiment, the second plurality of regions 34 may be equally spaced apart from each other along the first surface 16. In other embodiments, the second plurality of regions 34 may be randomly spaced throughout the monolayer 30 along the first surface 16. In still other embodiments, the second plurality of regions 34 may be arranged in a pattern within the monolayer 30. The second plurality of regions 34 may be present in the film 14 in an amount of from about 10 parts by volume to about 85 parts by volume based on 100 parts by volume of the film 14, e.g., about 25 parts by volume based on 100 parts by volume of the film 14.

The silver may be characterized as a nanoparticle and may have an average diameter measureable on a nanometer scale. Alternatively, the silver may be characterized as a particle and may have an average diameter measureable on a micrometer scale. Generally, the silver may be present in the film 14 in an amount of from about 2 parts by volume to about 35 parts by volume based on 100 parts by volume of the film 14. The silver may provide the film 14 with soil-resistance, anti-microbial, and air-purifying properties. For example, the silver may disrupt microbe cellular function. In particular, the silver may contribute to phospholipid decomposition such that a microbe cell wall cannot undergo respiration.

As best shown in FIG. 2, the film 14 defines a contact angle 36 with water of greater than 140°. For example, the film 14 may define a contact angle 36 with water of greater than or equal to 150°. As such, water, oils, and contaminants 100 may effectively bead on and translate across the first surface 16. Stated differently, water, oils, and contaminants 100 may be mobile and effectively translate along the first surface 16.

Figure 4:
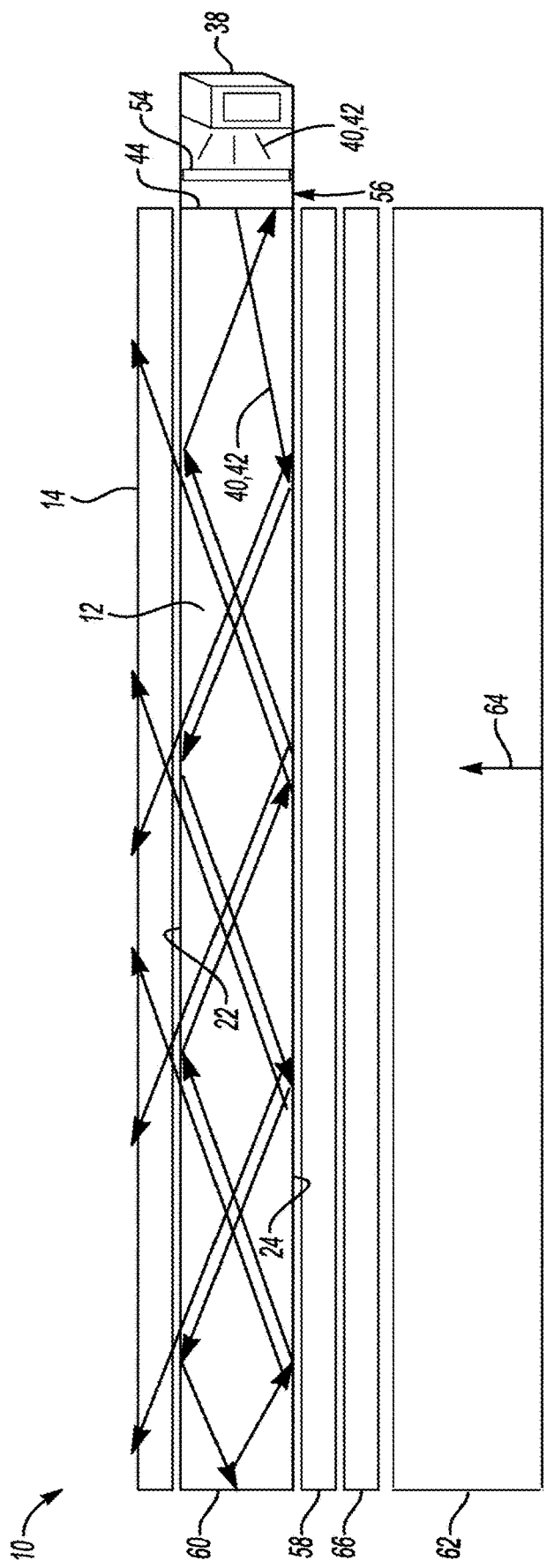
FIG. 4 is a schematic illustration of an exploded side view of the self-cleaning film system of FIGS. 1 and 2.

Referring now to FIG. 4, the self-cleaning film system 10 also includes a wave guide 38 disposed adjacent the substrate 12. For example, the wave guide 38 may be disposed along at least one of the first edge 26 (FIG. 2) and the second edge 28 (FIG. 2). In particular, and as set forth in more detail below, the wave guide 38 may inject a first portion 40 (FIG. 3) and a second portion 42 (FIG. 3) of electromagnetic radiation just below the film 14 at the substrate 12. That is, the wave guide 38 may be configured for emitting electromagnetic radiation 40, 42 towards the substrate 12 and therefore may be attached to the substrate 12.

For example, the self-cleaning film system 10 may further include an optical cement 44 disposed between the substrate 12 and the wave guide 38 such that the wave guide 38 may be adhered to the substrate 12. The optical cement 44 may be selected to allow transmittal of electromagnetic radiation 40, 42 (FIG. 3) through the optical cement 44 and to allow for precise positioning of the wave guide 38 on the substrate 12. A suitable optical cement 44 may include an optical epoxy commercially available under the tradename NOA from Norland Products, Inc. of Cranbury, N.J.

The wave guide 38 may be configured for adding electromagnetic radiation to the self-cleaning film system 10. For example, the wave guide 38 may ensure that the self-cleaning film system 10 may be operable in sheltered, shaded, or dark conditions in which the film 14 would otherwise be shielded from electromagnetic radiation having an ultraviolet or infrared wavelength.

In particular, referring now to FIG. 3, the wave guide 38 includes a first light source 46 configured for emitting the first portion 40 of electromagnetic radiation towards the film 14. The first portion 40 of electromagnetic radiation has an ultraviolet wavelength of from 10 nm to 400 nm. The first light source 46 may include a plurality of ultraviolet photodiodes 48. The wave guide 38 also includes a second light source 50 configured for emitting the second portion 42 of electromagnetic radiation towards the film 14. The second portion 42 of electromagnetic radiation has an infrared wavelength of from 700 nm to 1 mm. The second light source 50 may include a plurality of infrared photodiodes 52. As such, the wave guide 38 may be configured for emitting both ultraviolet electromagnetic radiation and infrared electromagnetic radiation towards the film 14.

Referring again to FIG. 4, the wave guide 38 may also include a diffuser 54 disposed at the substrate 12 and configured for diffusing the first portion 40 of electromagnetic radiation and the second portion 42 of electromagnetic radiation. For example, the diffuser 54 may include a plurality of diffusive structures (not shown) such as baffles disposed at an outlet 56 of the wave guide 38 near the substrate 12. The diffuser 54 may therefore interrupt or redirect or diffuse a transmission of the first portion 40 and second portion 42 of electromagnetic radiation from the first light source 46 (FIG. 3) and the second light source 50 (FIG. 3), respectively, to and through the substrate 12.

In addition, the self-cleaning film system 10 may also include a dielectric coating 58 disposed on the distal surface 24 and configured for reflecting the first portion 40 of electromagnetic radiation towards the proximal surface 22. That is, the dielectric coating 58 may be formed from a plurality of layers (not shown) and may reflect ultraviolet electromagnetic radiation back into the substrate 12. For example, the dielectric coating 58 may be a multilayer reflector configured for redirecting the first portion 40 of electromagnetic radiation towards the film 14.

Similarly, as best shown in FIG. 4, the self-cleaning film system 10 may further include a reflective tape 60 disposed along at least one of the first edge 26 (FIG. 2) and the second edge 28 (FIG. 2) of the substrate 12. The reflective tape 60 may likewise reflect ultraviolet electromagnetic radiation back into the substrate 12 towards the film 14 so that the first portion 40 of electromagnetic radiation may not escape from the substrate 12 through the first edge 26, the second edge 28, and the distal surface 24. A suitable reflective tape 60 may be commercially available under the tradename Silverlux® from 3M of St. Paul, Minn.

Referring now to FIGS. 3 and 4, the self-cleaning film system 10 may also include a display 62 configured for emitting a light ray 64 (FIG. 4) towards the substrate 12. The display 62 may project or emit the light ray 64 to the substrate 12 and film 14. The dielectric coating 58 may be sandwiched between the substrate 12 and the display 62. For example, the self-cleaning film system 10 may include an optical clear adhesive 66 such that the display 62 is adhered to the dielectric coating 58. As set forth above, the dielectric coating 58 may be configured for reflecting the first portion 40 of electromagnetic radiation towards the film 14. Since the wave guide 38 may inject the first portion 40 and the second portion 42 of electromagnetic radiation just below the film 14 at the substrate 12, the self-cleaning film system 10 may not require transmission of the first portion 40 and the second portion 42 through various layers 68, 70, 72, 78 (FIG. 3) of the display 62.

The display 62 may be, by way of non-limiting examples, a liquid crystal display, an organic light emitting diode display, or an opaque surface. In one non-limiting example, the display 62 may be a liquid crystal display disposed within a housing and configured for emitting an image. Although not shown, the display 62, e.g., the liquid crystal display, may include a light source, such as a white light emitting diode. The display may optically modulate the light ray 64 (FIG. 4) and emit the image, which may eventually be visible to an operator as text, a diagram, an object, a shape, and the like. For example, the image may be visible to the operator as a speed of travel, driving directions, ambient temperature data, a warning, a level indicator, text, and the like.

The display may include a passive matrix display arrangement or an active matrix display arrangement, i.e., a thin film transistor display arrangement. The passive matrix display arrangement may include a grid of conductors having one of a plurality of individual pixels disposed at each intersection in the grid. An electrical current may be transmitted across two conductors to control the operation and light of an individual pixel. Alternatively, the active matrix display arrangement may include a transistor at each intersection.

As shown in FIG. 3, the display 62 may include a first panel 68, which may include one or more polarizers 70 configured for polarizing visible light, i.e., electromagnetic radiation having a wavelength in the visible spectrum. More specifically, the display 62 may include a projector (not shown) configured for emitting the light ray 64 (FIG. 4). The light ray 64 may be polarized light. In particular, the light ray 64 may have an s-polarization state or a p-polarization state. Although not shown, the display 62 may include a suitable light source arranged to emit the light ray 64. For example, the display 62 may include optics to focus, magnify, refract, and/or reflect light, and may define one or more apertures. In a non-limiting example, the display 62 may emit the light ray 64 from a light-emitting diode.

With continued reference to FIG. 3, the display 62 may also include one or more optical foils 72 disposed adjacent the first panel 68. Suitable optical foils may enhance a brightness or clarity of the image and may be include a brightness enhancement film, a dual brightness enhancement film, a plurality of quantum dots, and combinations thereof.

Referring again to FIG. 3, the self-cleaning film system 10 may further include a third light source 74 disposed adjacent the display and configured for emitting a third portion 76 of electromagnetic radiation towards the display 62. For example, the display 62 may be a plastic encapsulated liquid crystal display and the third light source 74 may be a light emitting diode matrix backlight. More specifically, the display 62 may include a second panel 78 disposed adjacent the optical foil 72 and configured for channeling or guiding the third portion 76 of electromagnetic radiation towards the substrate 12. In one non-limiting example, the third light source 74 may be an ultraviolet light-emitting diode and the third portion 76 of electromagnetic radiation may have a wavelength of from 400 nm to 100 nm. Alternatively, the third light source 74 may be an incandescent bulb or a visible light-emitting diode and the third portion 76 of electromagnetic radiation may have a wavelength of from 740 nm to 380 nm.

Figure 5:
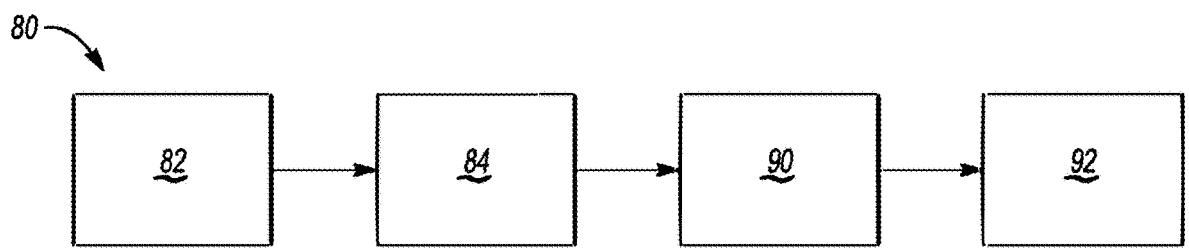
FIG. 5 is a flowchart of one embodiment of a method of forming the self-cleaning film system of FIGS. 1 and 2.

Referring now to FIG. 5, a method 80 of forming the self-cleaning film system 10 is illustrated generally. The method 80 includes depositing 82 the monolayer 30 formed from the fluorinated material selected from the group consisting of fluorinated organic compounds, fluorinated inorganic compounds, and combinations thereof onto the substrate 12. By way of non-limiting examples, depositing 82 may include chemical vapor depositing (CVD), physical vapor deposition (PVD), atomic layer deposition (ALD), dipping, wiping, spraying, meniscus coating, wet coating, combinations thereof, and the like. Depositing 82 may include forming a self-aligned monolayer 30 that is physically adsorbed, i.e., physisorbed, and cross-linked with neighboring molecules. In one example, depositing 82 may include magnetron sputter depositing a graphite target and a polytetrafluoroethylene target, i.e., co-sputtering. In another example, depositing 82 may include reactive magnetron sputter depositing graphite and polytetrafluoroethylene in a fluorine-containing gas, such as, but not limited to, difluoroacetylene gas, octafluorocyclobutane gas, tetrafluoromethane gas, and hexafluoropropylene oxide gas, which may contribute to a superhydrophobicity of the film 14.

That is, the monolayer 30 may be deposited in a suitable manner onto the substrate 12 such that the monolayer 30 chemically or physically bonds to the substrate 12. For example, for embodiments in which the substrate 12 is formed from silicon dioxide, each molecule of fluorinated material may be crosslinked to adjacent molecules of fluorinated material and new chemical bonds may be generated at the proximal surface 22 (FIG. 2) as the monolayer 30 is deposited onto the substrate 12.

After depositing 82, the method 80 may include ablating 84 the monolayer 30 to define a first plurality of cavities 86 (FIG. 3), wherein each of the first plurality of cavities 86 is spaced apart from an adjacent one of the first plurality of cavities 86 along the monolayer 30. In another embodiment, ablating 84 the monolayer 30 may also define a second plurality of cavities 88 (FIG. 3), wherein each of the second plurality of cavities 88 is spaced apart from an adjacent one of the second plurality of cavities 88 along the monolayer 30. As non-limiting examples, ablating 84 may include laser ablating, plasma ablating, ultraviolet ablating, and the like. Ablating 84 may remove several molecules of the fluorinated material monolayer 30 along the proximal surface 22 (FIG. 2) to define the first plurality of cavities 86. Similarly, ablating 84 may remove several molecules of the fluorinated material monolayer 30 along the proximal surface 22 to define the second plurality of cavities 88. Generally, the first plurality of cavities 86 may extend from the first surface 16 (FIG. 2) of the film 14 to the second surface 18 (FIG. 2) of the film 14. Similarly, the second plurality of cavities 88 may extend from the first surface 16 of the film 14 to the second surface 18 of the film 14.

After ablating 84, the method 80 may include embedding 90 the photocatalytic material into each of the first plurality of cavities 86 to form the film 14 on the substrate 12 and thereby form the self-cleaning film system 10. Therefore, the film 14 includes the first plurality of regions 32 (FIG. 3) including the photocatalytic material. The first plurality of regions 32 are disposed within the monolayer 30 and spaced apart from one another such that each of the first plurality of regions 32 abuts, is surrounded by, and is not covered by the fluorinated material. Similarly, the method 80 may include embedding 90 silver into each of the second plurality of cavities 88 to form the film 14 on the substrate 12. Therefore, the film 14 may include the second plurality of regions 34 (FIG. 3) including silver and disposed within the monolayer 30 such that each of the second plurality of regions 34 abuts and is surrounded by the silver. The second plurality of regions 34 may also not be covered by the fluorinated material.

Embedding 90 may include implanting or arranging the photocatalytic material into the monolayer 30 such that the photocatalytic material forms pillars within the first plurality of regions 32 (FIG. 3). For example, embedding 90 may include covering portions of the monolayer 30 with a mask (not shown) such that photocatalytic material is solely embedded into the first plurality of cavities 86 and is not deposited on top of the monolayer 30. Suitable processes for embedding 90 the photocatalytic material into the first plurality of cavities 86 (FIG. 3) to form the first plurality of regions 32 surrounded by the monolayer 30 include, but are not limited to, ion beam deposition, atomic layer deposition, chemical vapor deposition, physical vapor deposition, chemical precipitation, electrophoresis deposition, sputtering, co-sputtering, ion implantation, evaporation, co-evaporation, and pulsed laser deposition.

Embedding 90 may also include implanting or arranging silver into the monolayer 30 such that the silver forms pillars within the second plurality of regions 34 (FIG. 3). For example, embedding 90 may include covering portions of the monolayer 30 with the mask such that silver is solely embedded into the second plurality of cavities 88 (FIG. 3) and is not deposited on top of the monolayer 30. Suitable processes for embedding 90 silver into the second plurality of cavities 88 to form the second plurality of regions 34 surrounded by the monolayer 30 include, but are not limited to, ion beam deposition, atomic layer deposition, chemical vapor deposition, physical vapor deposition, chemical precipitation, electrophoresis deposition, sputtering, co-sputtering, ion implantation, evaporation, co-evaporation, and pulsed laser deposition.

In another embodiment, although not shown, the method 80 includes concurrently chemisorbing the fluorinated material and the functionalized photocatalytic material onto the substrate 12 to form the film 14 chemically bonded to the substrate 12 and thereby form the self-cleaning film system 10. The film 14 thus includes the monolayer 30 formed from the fluorinated material, and the first plurality of regions 32 each formed from the functionalized photocatalytic material and each disposed within the monolayer 30 and spaced apart from one another such that each of the first plurality of regions 32 abuts, is surrounded by, and is not covered by the fluorinated material. That is, the fluorinated material and the functionalized photocatalytic material may be deposited onto the substrate 12, simultaneously adsorbed onto the substrate 12, and chemically bonded to the substrate 12. The proximal surface 22 (FIG. 2) of the substrate 12 may concurrently chemically react with the fluorinated material and the functionalized photocatalytic material to form the film 14.

After embedding 90 or concurrently chemisorbing, the film 14 includes the first plurality of regions 32 (FIG. 3) formed from the photocatalytic material and spaced apart from one another along the first surface 16. Such first regions 32 may be useful for removing fingerprints from the film 14 so that the film 14 exhibits self-cleaning capability. In another embodiment, the film 14 may include the second plurality of regions 34 (FIG. 3) formed from silver and spaced apart from one another along the first surface 16. Such second regions 34 may be useful for increasing the anti-fouling and anti-microbial properties of the film 14 and may assist with odor removal from an ambient environment.

Referring again to FIG. 5, the method 80 further includes irradiating 92 the film 14 with the second portion 42 (FIG. 3) of electromagnetic radiation, i.e., irradiating 92 the film 14 with infrared light, to thereby move the contaminant 100 (FIG. 1) towards the first plurality of regions 32 (FIG. 3), as set forth in more detail below. That is, irradiating 92 may include at least one of stretching, deforming, and rocking the methyl group 102 (FIG. 1) of the contaminant 100 so that the contaminant 100 translates along the film 14. For example, irradiating 92 may increase a motion of the contaminant 100 along the first surface 16 of the film 14 and may consequently increase a likelihood of the contaminant 100 encountering at least one of the first plurality of regions 32 formed from photocatalytic material.

In particular, irradiating 92 may include exposing the contaminant 100 to electromagnetic radiation having a wavelength that induces vibration of the at least one methyl group 102 (FIG. 1). For example, irradiating 92 may include stretching the at least one methyl group 102 by exposing the contaminant 100 to the second portion 42 of electromagnetic radiation. Likewise, irradiating 92 may include deforming the at least one methyl group 102 by exposing the contaminant 100 to the second portion 42 of electromagnetic radiation. Similarly, irradiating 92 may include rocking the at least one methyl group 102 by exposing the contaminant 100 to the second portion 42 of electromagnetic radiation. Such stretching, deforming, and/or rocking may translate or wiggle the contaminant 100 along the film 14.

The method 80 further includes irradiating 92 the film 14 with the first portion 40 of electromagnetic radiation, i.e., irradiating 92 the film 14 with ultraviolet light, to thereby increase a photocatalytic degradation of the contaminant 100 at the first plurality of regions 32 (FIG. 3) and reduce the visibility of the contaminant 100, as also set forth in more detail below. That is, irradiating 92 may increase a photocatalytic activity of the photocatalytic material at the first plurality of regions 32.

More specifically, the irradiating 92 may include emitting electromagnetic radiation having a wavelength tuned to a bandgap of the photocatalytic material to initiate photocatalysis of the contaminant 100, e.g., squalene deposited as a fingerprint, as set forth in more detail below. As used herein, the terminology bandgap refers to a difference in energy between the highest permitted energy level for an electron in a valence band of the photocatalytic material and the lowest permitted energy level in a conduction band of the photocatalytic material. In other words, the bandgap refers to the minimum amount of light required to make the photocatalytic material electrically conductive.

The method 80 may further include contacting the film 14 and the contaminant 100, e.g., squalene having the methyl groups 102 (FIG. 1). That is, contacting may include touching the film 14 such that an operator deposits the contaminant 100, e.g., fingerprints, squalene, organic matter, and/or oils onto the first surface 16 (FIG. 2). Oils may include oils of fatty acids and may be synthesized naturally and applied to the film 14 as the operator touches the film 14, or may be applied to the film 14 artificially such as by spraying or coating. Contact between the contaminant 100 and the photocatalytic material which is exposed to electromagnetic radiation emitted by the wave guide 38 may initiate a photocatalytic reaction. More specifically, the photocatalytic material may be a photocatalyst such as titanium dioxide or titanium dioxide doped with silver. The photocatalytic reaction may create a strong oxidation agent and breakdown the contaminant 100, e.g., organic matter or squalene, to carbon dioxide and water in the presence of the photocatalyst, i.e., the photocatalytic material; electromagnetic radiation, e.g., ultraviolet light; and water, e.g., humidity from ambient conditions. As such, the photocatalytic material not be consumed by the catalytic reaction, but may instead solely accelerate the photocatalytic reaction as a non-reactant.

In greater detail, when electromagnetic radiation having a desired wavelength illuminates the photocatalytic material, e.g., titanium dioxide, titanium dioxide doped with silver, or a mixture of titanium dioxide nanoparticles and silver nanoparticles, an electron from the valence band of the photocatalytic material may promote to the conduction band of the photocatalytic material, which in turn may create a hole in the valence band and an excess of negative charge or electron in the conduction band. The hole may assist oxidation and the electron may assist reduction. Generally, the hole may combine with water to produce a hydroxyl radical (.OH). The hole may also react directly with the contaminant 100 to increase an overall self-cleaning efficiency of the film 14. Similarly, oxygen in the ambient environment surrounding the photocatalytic material may be reduced by the electron to form a superoxide ion ($.O_2$—), which in turn may oxidize the organic material present on the film 14. Therefore, the method 80 may include oxidizing the contaminant 100. For embodiments including silver, the hydroxyl radical may also decompose a phospholipid portion of a microbe cellular wall and cytoplasm wall such that the microbe dies from lack of respiration, which may decompose organic matter present on the film 14 and contribute to anti-fouling and anti-staining properties of the film 14.

In addition, the hole may become trapped before recombination with the electron. For such situations, the photocatalytic material may be functionalized. For example, the method 80 may include doping titanium dioxide with, for example, palladium or ruthenium. The palladium or ruthenium may act as an electrocatalyst and may increase a transfer of electrons to oxygen molecules, which may in turn lower the occurrence of the recombination of electrons and holes.

Further, organic material that is present on the film 14 at the monolayer 30 rather than in direct contact with the first plurality of regions 32 may be in dynamic equilibrium with the first surface 16 (FIG. 2) and may diffuse toward a comparatively higher-energy location on the film 14, i.e., the first plurality of regions 32. Therefore, the method 80 may also include diffusing the contaminant 100 along the film 14 from the monolayer 30 to at least one of the first plurality of regions 32. To improve such diffusion, the wave guide 38, e.g., the first light source 46 and the second light source 50, may be tuned to emit electromagnetic radiation having a wavelength that is tuned to a vibration resonance of the contaminant 100 and the fluorinated material. Such tuning may enable the contaminant 100 or fingerprint to wiggle or translate along the monolayer 30 to the first plurality of regions 32 where the contaminant 100 may undergo the photocatalytic reaction described above. Alternatively or additionally, the film 14 may also be heated, for example by infrared radiation, to further improve diffusion across the monolayer 30 towards the first plurality of regions 32.

As such, the method 80 may further include vaporizing the contaminant 100. More specifically, once the contaminant 100 contacts the photocatalytic material at the first plurality of regions 32, the contaminant 100 may be photolyzed into comparatively low vapor pressure-sized pieces or parts, which may vaporize off the film 14 and thereby remove the contaminant 100 or squalene from the film 14. Therefore, the self-cleaning film system 10 may be characterized as self-cleaning. That is, the film 14 may protect the substrate 12 by removing, e.g., oxidizing and vaporizing, the contaminant 100, e.g., fingerprints, squalene, oils, and/or organic material, deposited by the touch of an operator. Consequently, the self-cleaning film system 10 and method 80 may provide excellent aesthetics, cleanliness, and readability for display systems, lenses, sensors, and surfaces especially for applications in which the self-cleaning film system 10 is shielded from ultraviolet or infrared wavelengths of electromagnetic radiation by, for example, tinted glass. In particular, the film 14 may be comparatively thin, super hydrophobic, transparent, scratch-resistant, durable, tough, and may be a hard coating, i.e., may have a hardness of greater than 17.5 GPa and an elastic modulus of greater than 150 GPa.

While the best modes for carrying out the disclosure have been described in detail, those familiar with the art to which this disclosure relates will recognize various alternative designs and embodiments for practicing the disclosure within the scope of the appended claims.

What is claimed:

1. A self-cleaning film system comprising:
   a substrate;
   a film disposed on the substrate and including:
   a monolayer formed from a fluorinated material selected from the group consisting of fluorinated organic compounds, fluorinated inorganic compounds, and combinations thereof; and
   a first plurality of regions disposed within the monolayer and spaced apart from one another such that each of the first plurality of regions abuts, is surrounded by, and is not covered by the fluorinated material, wherein each of the first plurality of regions includes a light-activated photocatalytic material; and
   a wave guide disposed adjacent the substrate comprising at least one source of light configured to transmit electromagnetic radiation towards the film.

2. The self-cleaning film system of claim 1, wherein the at least one source of light is selected from the group consisting of:
   a first light source configured for emitting electromagnetic radiation having an ultraviolet wavelength;
   a second light source configured for emitting electromagnetic radiation having an infrared wavelength;
   a third light source configured for emitting electromagnetic radiation having a visible light wavelength; and combinations thereof.

3. The self-cleaning film system of claim 1, wherein the at least one source of light comprises a plurality of ultraviolet light emitting diodes, a plurality of infrared light emitting diodes, or both a plurality of ultraviolet light emitting diodes and a plurality of infrared light emitting diodes.

4. The self-cleaning film system of claim 1, wherein the film has a first surface and a second surface spaced opposite the first surface and abutting the substrate, wherein the substrate has:
   a proximal surface abutting the second surface;
   a distal surface spaced opposite the proximal surface;
   a first edge connecting the proximal surface and the distal surface; and
   a second edge spaced opposite the first edge; and
   wherein the wave guide is disposed adjacent the first edge.

5. The self-cleaning film system of claim 4, further including a dielectric coating disposed on the distal surface and configured for reflecting the electromagnetic radiation towards the proximal surface.

6. The self-cleaning film system of claim 1, wherein the film has a first surface and a second surface spaced opposite the first surface and abutting the substrate, and further wherein the first surface is substantially free from squalene.

7. The self-cleaning film system of claim 1, wherein the light-activated photocatalytic material is functionalized with a dopant selected from the group consisting of silver, chromium, cobalt, tungsten, copper, vanadium, iron, platinum, molybdenum, lanthanum, niobium, nitrogen, sulfur, carbon, boron, potassium, iodine, fluorine, and combinations thereof.

8. The self-cleaning film system of claim 1, wherein the light-activated photocatalytic material comprises titanium dioxide.

9. The self-cleaning film system of claim 8, wherein the titanium dioxide is present in the first plurality of regions in a rutile form, an anatase form, or a combination of a rutile form and an anatase form.

10. The self-cleaning film system of claim 1, wherein the light-activated photocatalytic material comprises titanium dioxide doped with silver.

11. A self-cleaning film system comprising:
    a substrate;
    a film disposed on the substrate and including:
    a monolayer formed from a fluorinated material selected from the group consisting of fluorinated organic compounds, fluorinated inorganic compounds, and combinations thereof; and
    a first plurality of regions disposed within the monolayer and spaced apart from one another such that each of the first plurality of regions abuts, is surrounded by, and is not covered by the fluorinated material, wherein each of the first plurality of regions includes a light-activated photocatalytic material; and
    a wave guide disposed adjacent the substrate comprising at least one source of light configured to transmit electromagnetic radiation towards the light-activated photocatalytic material in the film, wherein the electromagnetic radiation is in a range of ultraviolet wavelengths, infrared wavelengths, or visible light wavelengths.

12. The self-cleaning film system of claim 11, wherein the at least one source of light comprises a first light source configured for emitting electromagnetic radiation having an ultraviolet wavelength; and a second light source configured for emitting electromagnetic radiation having an infrared wavelength or emitting electromagnetic radiation having a visible light wavelength.

13. The self-cleaning film system of claim 11, wherein the at least one source of light comprises a plurality of light emitting diodes.

14. The self-cleaning film system of claim 11, wherein the at least one source of light comprises a matrix of light emitting diodes.

15. The self-cleaning film system of claim 11, wherein the light-activated photocatalytic material comprises titanium dioxide functionalized with a dopant selected from the group consisting of silver, chromium, cobalt, tungsten, copper, vanadium, iron, platinum, molybdenum, lanthanum, niobium, nitrogen, sulfur, carbon, boron, potassium, iodine, fluorine, and combinations thereof.

16. A self-cleaning film system comprising:
a substrate;
a film disposed on the substrate and including:
   a monolayer formed from a fluorinated material comprising fluorinated diamond like carbon (F-DLC); and
   a first plurality of regions disposed within the monolayer and spaced apart from one another such that each of the first plurality of regions abuts, is surrounded by, and is not covered by the fluorinated material, wherein each of the first plurality of regions includes a light-activated photocatalytic material comprising titanium dioxide; and
at least one light source configured to transmit electromagnetic radiation having an ultraviolet wavelength towards the light-activated photocatalytic material in the film.

17. The self-cleaning film system of claim 16, further comprising a second light source configured for emitting electromagnetic radiation either having an infrared wavelength or a visible light wavelength.

18. The self-cleaning film system of claim 16, wherein the light-activated photocatalytic material comprising titanium dioxide is functionalized with a dopant selected from the group consisting of silver, chromium, cobalt, tungsten, copper, vanadium, iron, platinum, molybdenum, lanthanum, niobium, nitrogen, sulfur, carbon, boron, potassium, iodine, fluorine, and combinations thereof.

19. The self-cleaning film system of claim 16, further comprising a wave guide disposed adjacent the substrate.

* * * * *